(12) United States Patent
Hayat et al.

(10) Patent No.: US 7,851,639 B2
(45) Date of Patent: Dec. 14, 2010

(54) METHOD FOR THE PRODUCTION OF A-(ALPHA-HYDROXYALKYL)-1,3 DIOXAN-5-ONES

(75) Inventors: Nasir Hayat, Bielefeld (DE); Meinolf Lange, Bielefeld (DE); Fritz Link, Bensberg (DE); Christiane Neuhaus, Halle/Saale (DE); Bernhard Westermann, Halle/Saale (DE)

(73) Assignee: Girindus AG, Bergisch-Gladbach (DE)

( * ) Notice: Subject to any disclaimer, the term of this patent is extended or adjusted under 35 U.S.C. 154(b) by 797 days.

(21) Appl. No.: 11/629,772

(22) PCT Filed: Jun. 15, 2005

(86) PCT No.: PCT/EP2005/052757

§ 371 (c)(1), (2), (4) Date: Aug. 8, 2007

(87) PCT Pub. No.: WO2005/123712

PCT Pub. Date: Dec. 29, 2005

(65) Prior Publication Data

US 2008/0097113 A1    Apr. 24, 2008

(30) Foreign Application Priority Data

Jun. 15, 2004    (EP)    ................... 04102730

(51) Int. Cl.
C07D 319/06    (2006.01)

(52) U.S. Cl. ..................................... 549/372
(58) Field of Classification Search .................. 549/372
See application file for complete search history.

(56) References Cited

PUBLICATIONS

Majeweski et al., J. org Chem. (2000), vol. 65(17), pp. 5152-5160.*
Wu et al., Helv. Chim. Acta, (2004), vol. 87(6), pp. 1377-1384.*

* cited by examiner

*Primary Examiner*—Taofiq A Solola
(74) *Attorney, Agent, or Firm*—Connolly Bove Lodge & Hutz LLP

(57) ABSTRACT

A process for the synthesis of compounds of general formulas

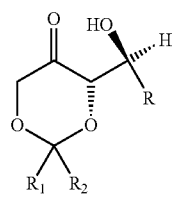

1

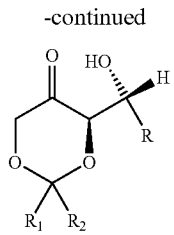

2

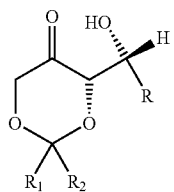

3

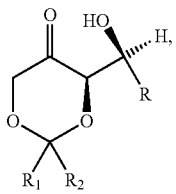

4 comprising the step of reacting

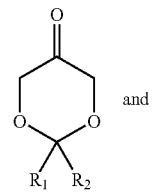

5 and

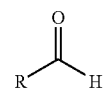

6 in the presence of

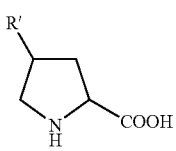

7 wherein:
R=substituted or unsubstituted alkyl, aryl, heterocycles containing one or more O, N, S, P or B;
$R_1$ and $R_2$ independently represent H, substituted or unsubstituted alkyl, aryl, heterocycles containing one or more O, N, S, P or B;
R'=H, OH, OR or $OSiX_3$, wherein X independently represent alkyl or aryl.

8 Claims, No Drawings

METHOD FOR THE PRODUCTION OF A-(ALPHA-HYDROXYALKYL)-1,3 DIOXAN-5-ONES

RELATED APPLICATIONS

This application is a national stage application (under 35 U.S.C. §371) of PCT/EP2005/052757, filed Jun. 15, 2005, which claims benefit of European application 04102730.1, filed Jun. 15, 2004.

The present invention relates to a synthetic process and to compounds obtainable thereby.

Aldol reactions are among the essential carbon-carbon bond formation reactions both in nature and in the repertoire of the synthetic chemist. In nature, such reactions are catalyzed by enzymes which function through either an enamine mechanism (class 1 aldolases) or a zinc cofactor (class 2 aldolases). A high stereoselectivity is achieved.

Despite the pioneering developments of the stereoselective metal-catalyzed aldol reaction in recent years (see "Comprehensive Asymmetric Catalysis"; Chapter 29, ed. Eric N. Jacobsen, Andreas Pflatz, Hisahi Yamamoto, Springer Verlag, Berlin, 2002), successes by means of organocatalytic methods with a wide substrate range could be presented only recently.

However, all these methods give poor yields and selectivities if the natural phosphorylated substrate of the aldolases, dihydroxyacetone (DHA), is employed.

In Tetrahedron Letters 31 (2000) 5909-5913, Kwan Soo Kim et al. describe a process for the preparation of dihydroxyacetone derivatives via dihydroxyacetone silylenol ether and subsequent aldol reaction. The reaction comprises an organometallic conversion with lithium diisopropylamide at −78° C.

In J. Org. Chem. 65 (2000) 5152-5160, Marek Majewski et al. describe a process for the aldol reaction of enolates from 1,3-dioxane-5-ones by reacting them with chiral lithium amides.

Corresponding aldol reactions with cyclic secondary amines in organic solvents and aqueous media have been known; cf. A. Córdova, W. Notz and C. F. Barbas III. in Chem. Commun. 2002, pages 3024 to 3025. The stereoselectivities observed therein are predominantly low.

It was the object of the present invention to develop an improved synthetic process with a high stereoselectivity on the basis of aldol reactions.

This object is achieved by a process for the synthesis of compounds of general formulas

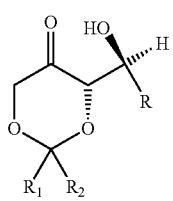

1

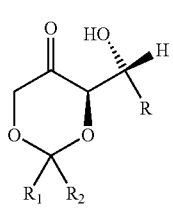

2

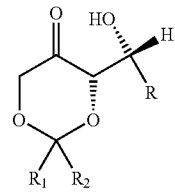

3

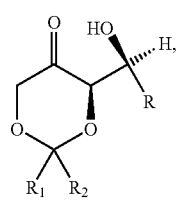

4 comprising the step of reacting

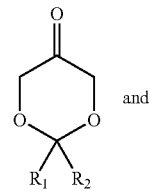

5 and

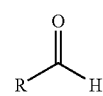

6 in the presence of

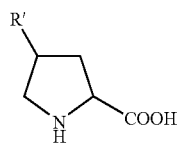

7 wherein:

R=substituted or unsubstituted alkyl, aryl, heterocycles containing one or more O, N, S, P or B;

$R_1$ and $R_2$ independently represent H, substituted or unsubstituted alkyl, aryl, heterocycles containing one or more O, N, S, P or B;

R'=, OH, OR or $OSiX_3$, wherein X independently represent alkyl or aryl.

According to the invention, a cyclic starting compound is employed, namely derivatives of 1,3-dioxan-5-one, which are reacted in the presence of proline or proline derivatives with aldehydes. These starting compounds are dihydroxyacetone derivatives. High stereoselectivities are achieved.

Presumably, the proline or proline derivative forms an enamine intermediate in which the carboxy group of proline participates in the orientation to thereby achieve the surprisingly high stereoselectivities.

"Alkyl" within the meaning of this application means, in particular, straight or branched chain alkyl, cycloalkyl, bicycloalkyl, tricycloalkyl, alkenyl, alkynyl, heterocycloalkyl compounds. Typical representatives are methyl, ethyl, n-propyl, isopropyl, butyl, cyclohexyl or substituted derivatives thereof.

"Aryl" within the meaning of this application includes, in particular, heteroaryl, arylalkyl or heteroarylalkyl groups. Typical representatives are phenyl, benzyl, pyridine and substituted derivatives thereof.

Said alkyl or aryl residues may also be derivatives substituted with one or more hydroxy, alkoxy, aryloxy, alkanoyl, aroyl, carboxy, alkoxycarbonyl, amino, alkylamino, hydroxylamino, amido, carbamoyl, ureido, amidino, guanidino, cyano, azido, mercapto, alkylthio, alkylsulfoxy, alkylsulfonyl, alkylsulfenyl, aminosulfonyl, fluoro, chloro, bromo, iodo, alkyl or perfluoroalkyl residues.

In a preferred embodiment, R contains one or more nitrogen atoms. In this case, the compounds are derivatives of compounds with, for example, azetidine, pyrrolidine, pyrroline, piperidine, piperazine, homopiperazine, morpholine, thiomorpholine, pyridine, di- or tetrahydropyridine, pyrimidine, pyrazine, azepine, dihydroazepine, oxazepine, diazepine, imidazole, pyrazole, oxazole or thiazole rings optionally having anellated aliphatic, heteroaliphatic, aromatic or heteroaromatic rings and/or being substituted with one or more hydroxy, alkoxy, aryloxy, alkanoyl, aroyl, carboxy, alkoxycarbonyl, amino, alkylamino, hydroxylamino, amido, carbamoyl, ureido, amidino, guanidino, cyano, azido, mercapto, alkylthio, alkylsulfoxy, alkylsulfonyl, alkylsulfenyl, aminosulfonyl, fluoro, chloro, bromo, iodo, alkyl or perfluoroalkyl residues.

The amounts of proline or proline derivative necessary for the reaction are typically from 0.1 to 30 mole percent, more preferably from 1 to 10 mole percent, even more preferably from 1 to 5 mole percent.

The amount employed of proline or proline derivative participates in the reaction only catalytically and therefore can be recovered in principle.

To obtain compounds of structural formula 1, 3, the reaction is performed by means of proline. To obtain compounds 2, 4, D-proline is typically employed. Alternatively, 4-hydroxyproline or a protected precursor thereof may also be employed.

The ratio of formation of anti (1, 2) and syn (2, 4) compounds depends on the component of structural formula 6.

In one embodiment, the reaction is performed in an aqueous solvent. In this case, the proportion of water is preferably more than 50%, more preferably more than 90%.

In another embodiment, the reaction is performed without a solvent.

Particular suitable solvents are trifluoroethanol and formamide, both optionally in admixture with water. Preferably, however, the proportion of water is below 20%. Further suitable solvents are DMSO and DMF. Of course, mixtures of these solvents may also be employed.

When trifluoroethanol is employed, an enantiomeric excess of >98% is typically achieved.

Particularly preferred residues R are those in which R=—CH(OH)—CH$_2$—N$_3$ (R or S) or 6

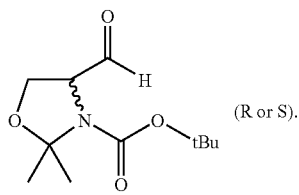

(R or S).

The invention further relates to the use of compound 5 as a reagent in an aldol reaction.

The invention further relates to compounds of general formula

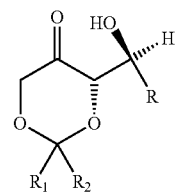

1

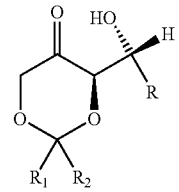

2

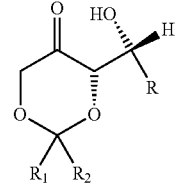

3

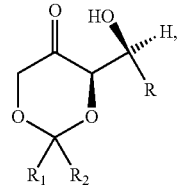

4 wherein:

R=substituted or unsubstituted alkyl, aryl, heterocycles containing one or more O, N, S, P or B;

R$_1$ and R$_2$ independently represent H, substituted or unsubstituted alkyl, aryl, heterocycles containing one or more O, N, S, P or B.

The substances according to the invention which can be obtained via the new synthetic route in high stereoselectivities are suitable, in particular, as starting materials or intermediates in the synthesis of carbohydrates and azacarbohydrates. Therefore, the invention also relates to the use of the compound according to the invention as an intermediate in the synthesis of carbohydrates or azacarbohydrates.

Upon cleaving off C(R$_1$R$_2$), for example, in an acidic medium, preferably by using acidic ion-exchangers, the dihydroxyacetone skeletal structure is recovered. It may undergo ring-closing reactions with the residue coupled by the aldol reactions. In embodiments in which R contains an amine, the amine may be used to form azasugars or aminosugars.

The invention is explained in more detail by the following further Examples.

EXAMPLES

General Protocol

A suspension of L-proline (20-30 mole percent), 5-oxo-1,3-dioxane 5 (1.0 mmol) and an aldehyde 6 (1.0 mmol) in DMSO (0-8 ml) was stirred at room temperature for 12 to 48 hours. After the starting material has been converted completely (as confirmed by thin-layer chromatography), the reaction mixture was processed by adding saturated ammonium chloride solution (3 ml), extracting with ethyl acetate and drying the organic phases over magnesium sulfate. The raw product was further purified by column chromatography on silica gel with heptane/ethyl acetate (3.1).

NMR Data (1'S,4S)-4-(1'-Hydroxy)propyl-2,2-dimethyl[1,3]dioxan-5-one

Yield: 56%

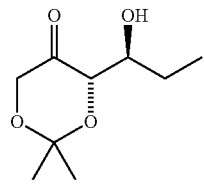

$^{1}$H NMR (250 MHz, CDCl$_{3}$): δ=0.97 (t, 3H), 1.45, 1.49 (2s, 6H), 1.51-1.81 (m, 2H), 3.05 (br s, 1H, OH), 3.80-3.88 (m, 1H), 3.98-4.13 (m, 2H), 4.20-4.34 (m, 1H);—
$^{13}$C NMR (50 MHz, CDCl$_{3}$): δ=9.6, 23.8, 24.2, 25.6, 67.1, 72.1, 76.0, 101.3, 211.8.—

(1'S,4S)-4-(1'-Hydroxy-3'-methyl)butyl-2,2-dimethyl[1,3]dioxan-5-one

Yield: 72%

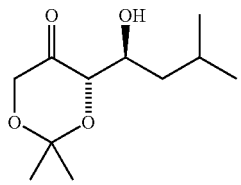

$^{1}$H NMR (250 MHz, CDCl$_{3}$): δ=0.85-0.98 (m, 8H), 1.40 (s, 3H), 1.43 (s, 3H), 1.72-1.94 (m, 1H), 2.99 (s, 1H, OH), 3.92-4.26 (m, 4H);—
$^{13}$C NMR (50 MHz, CDCl$_{3}$): δ=21.8, 23.8, 24.1 24.2, 41.5, 67.1, 69.6, 77.1, 101.2, 211.1.

(1'S,4S)-4-(1'-Hydroxy-1'-cyclohexyl)methyl-2,2-dimethyl[1,3]dioxan-5-one

Yield: 70%

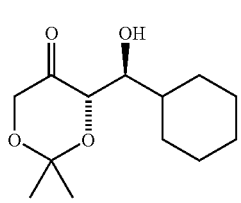

$^{1}$H NMR (250 MHz, CDCl$_{3}$): δ=1.01-1.33 (m, 5H), 1.44, 1.48 (2s, 6H), 1.55-1.89 (m, 6H), 3.11-3.24 (br s, 1H), 3.59-3.72 (m, 1H), 3.93-4.04 (m, 1H), 4.10-3.19 (m, 1H), 4.19-4.32 (m, 2H);—
$^{13}$C NMR (50 MHz, CDCl$_{3}$): δ=24.0, 24.2, 26.5, 26.6, 26.8, 29.9, 38.8, 67.0, 73.8, 74.6, 101.3, 212.5.

(1'S,4S)-4-(1'-Hydroxy-3'-phenyl)propyl-2,2-dimethyl[1,3]dioxan-5-one

Yield: 80%

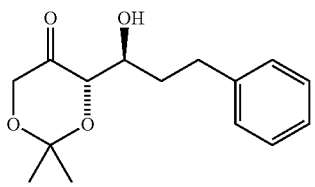

$^{1}$H NMR (250 MHz, CDCl$_{3}$): δ=1.48 (s, 3H), 1.51 (s, 3H), 1.78-2.11 (m, 2H), 2.56-2.83 (m, 1H), 2.88-3.09 (m, 1H), 3.18 (br s, 1H, OH), 3.83-4.35 (m, 3H), 7.13-7.45 (m, 5H);—
$^{13}$C NMR (50 MHz, CDCl$_{3}$): δ=24.0, 24.2, 31.8, 34.6, 67.1, 70.3, 76.4, 101.5, 126.3, 128.8, 129.0, 142.4, 211.6.

(1'S,4S)-4-(1'-Hydroxy-1'-phenyl)methyl-2,2-dimethyl[1,3]dioxan-5-one (anti)

(1'R,4S)-4-(1'-Hydroxy-1'-phenyl)methyl-2,2-dimethyl[1.3]dioxan-5-one (syn)

Yield: 77% (total yield of both diastereomers)
In this case, L-proline yielded both the anti and syn products. They could be separated by chromatography and showed the following NMR spectroscopy data:

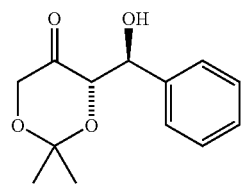

anti $^{1}$H NMR (250 MHz, CDCl$_{3}$): δ=1.29, 1.39 (2s, 6H), 3.63 (br s, 1H, OH), 3.92-4.39 (m, 3H), 4.82-4.95 (m, 1H), 7.34-7.51 (m, 5H);—
$^{13}$C NMR (50 MHz, CDCl$_{3}$): δ=23.6, 24.0, 67.1, 73.1, 76.6, 101.6, 127.5, 128.4, 139.7, 211.3.

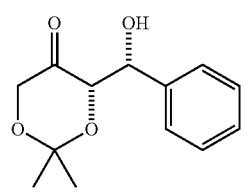

syn $^{1}$H NMR (250 MHz, CDCl$_{3}$): δ=1.38, 1.50 (2s, 6H), 3.99-4.49 (m, 3H), 5.02-5.20 (br s, 1H, OH), 5.26 (d, 1H, J=2.7 Hz), 7.22-7.64 (m, 5H);—
$^{13}$C NMR (50 MHz, CDCl$_{3}$): δ=23.7, 24.7, 67.6, 71.7, 78.6, 101.4, 126.9, 128.7, 130.5, 140.7, 208.3.

The invention claimed is:
1. A process for the synthesis of compounds of general formulas

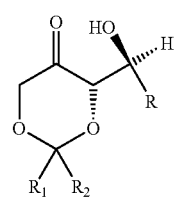

1

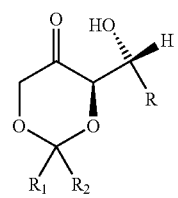

2

-continued

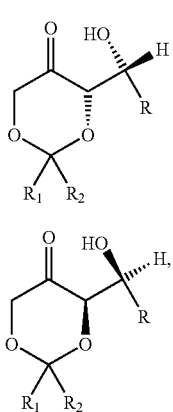

comprising the step of reacting compounds of general formulas

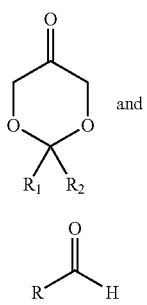

in the presence of a compound of general formula

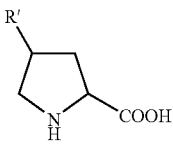

wherein:

R is substituted or unsubstituted alkyl, substituted or unsubstituted aryl, or substituted or unsubstituted heterocycle containing one or more O, N, S, P or B;

$R_1$ and $R_2$ are independently H, substituted or unsubstituted alkyl, substituted or unsubstituted aryl, or substituted or unsubstituted heterocycle containing one or more O, N, S, P or B;

R' is H, OH, OR or $OSiX_3$, wherein X is independently alkyl or aryl.

2. The process according to claim 1, wherein the compound of general formula 7 is present in an amount from 0.1 to 30 mole percent, based on the compound of general formula 5.

3. The process according to claim 1, wherein R contains one or more N.

4. The process according to claim 1, wherein the compound of general formula 6 is

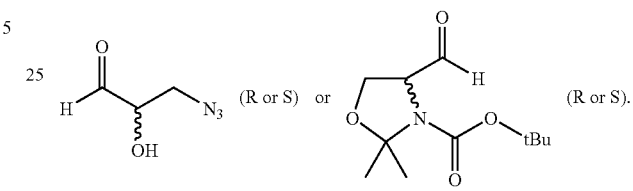

5. The process according to claim 1, wherein the reaction is performed in an aqueous solvent.

6. The process according to claim 1, wherein the reaction is performed without a solvent.

7. The process according to claim 1, wherein compounds of general formulas 1 and 3 are synthesized when the compound of general formula 7 is L-proline, and wherein compounds of general formulas 2 and 4 are synthesized when the compound of general formula 7 is D-proline.

8. The process according to claim 1, wherein the reaction is performed in a solvent comprising trifluoroethanol or formamide.

* * * * *